United States Patent [19]

Kobayashi

[11] 4,373,525
[45] Feb. 15, 1983

[54] METHOD AND APPARATUS FOR DETECTING OCCLUSION IN FLUID-INFUSION TUBE OF PERISTALTIC TYPE FLUID-INFUSION PUMP

[75] Inventor: Susumu Kobayashi, Fujinomiya, Japan

[73] Assignee: Terumo Corporation, Tokyo, Japan

[21] Appl. No.: 231,955

[22] Filed: Feb. 6, 1981

[30] Foreign Application Priority Data

Feb. 12, 1980 [JP] Japan .................. 55/15644

[51] Int. Cl.³ .................. A61M 5/00; F04B 49/00
[52] U.S. Cl. .................. 128/214 E; 128/214 F; 128/DIG. 12; 128/DIG. 13; 417/38; 417/63
[58] Field of Search ....... 128/214 E, 214 F, DIG. 12, 128/DIG. 13; 417/479, 63, 38; 73/716

[56] References Cited

U.S. PATENT DOCUMENTS

| | | | |
|---|---|---|---|
| 2,340,008 | 1/1944 | Matuszak | 73/716 |
| 2,483,924 | 10/1949 | Moulinier | 128/214 F |
| 3,731,680 | 5/1973 | Wright et al. | 128/214 F X |
| 4,210,138 | 7/1980 | Jess | 128/214 E |
| 4,212,591 | 7/1980 | Lamontagne et al. | 417/38 |
| 4,213,454 | 7/1980 | Shim | 128/214 E |
| 4,243,031 | 1/1981 | Genese | 128/214 E |
| 4,244,365 | 1/1981 | McGill et al. | 128/214 E |
| 4,256,437 | 3/1981 | Brown | 128/214 E X |
| 4,277,226 | 7/1981 | Archibald | 128/214 E X |

FOREIGN PATENT DOCUMENTS

54-90891 7/1979 Japan .

Primary Examiner—Kyle L. Howell
Assistant Examiner—John C. Hanley
Attorney, Agent, or Firm—Frishauf, Holtz, Goodman and Woodward

[57] ABSTRACT

A change in the internal pressure of the fluid-infusion tube of a peristaltic fluid-infusion pump due to occlusion in the fluid-infusion tube is detected through a change in the diameter of the fluid-infusion tube. The occlusion is detected by detection of the change in the distance between the opposite wall portions of the tube.

15 Claims, 15 Drawing Figures

METHOD AND APPARATUS FOR DETECTING OCCLUSION IN FLUID-INFUSION TUBE OF PERISTALTIC TYPE FLUID-INFUSION PUMP

BACKGROUND OF THE INVENTION

The present invention relates to a method and apparatus for detecting occlusion in a fluid-infusion tube of a peristaltic type fluid-infusion pump.

In performing fluid-infusion with an injection pump, smooth fluid infusion is obstructed an when occlusion of the fluid infusion line is formed at the inlet or outlet port of the pump. When an occlusion is formed at the outlet port, the internal pressure of the fluid-infusion line is raised by the delivery pressure of the pump. When this pressure exceeds the maximum pressure the fluid-infusion line can withstand, the fluid-infusion line may be broken, posing an extreme danger. In order to eliminate such a danger, fluid-infusion pumps are generally equipped with an apparatus for detecting occlusion of the pump. Conventionally, a volumetric pump of the cylinder type is provided with an apparatus for detecting the occlusion, while a peristaltic type pump is not provided with this apparatus.

SUMMARY OF THE INVENTION

It is, therefore, the primary object of the present invention to provide a method and apparatus for detecting occlusion in a fluid-infusion tube of a peristaltic type fluid-infusion pump.

According to one aspect of the present invention, there is provided a method for detecting occlusion in a fluid-infusion tube of a peristaltic type fluid-infusion pump according to which a change in the internal pressure of a peristaltic type fluid-infusion tube caused by occlusion in the fluid-infusion tube is detected through a change in a distance between opposite wall portions of the fluid-infusion tube, and the occlusion of the fluid-infusion tube is detected by the change in the distance between the opposite wall portions of the tube.

According to another aspect of the present invention, there is also provided an apparatus for detecting occlusion in a peristaltic type fluid-infusion pump comprising: a pair of stationary pieces respectively mounted at a fluid inlet portion and a fluid outlet portion of the peristaltic type fluid-infusion pump; a movable member having a pair of pressing parts disposed respectively in opposition to the stationary pieces and pressing an elastic fluid-infusion tube at a predetermined pressure in cooperation with the stationary pieces, the movable member being displaced by a change in a distance between opposite wall portions of the fluid-infusion tube which is in turn changed by a change in the internal pressure of the fluid-infusion tube caused by a closure in the fluid-infusion tube; and means for detecting the occlusion by detecting the displacement of the movable member.

DETAILED DESCRIPTION OF THE INVENTION

Figure 1:
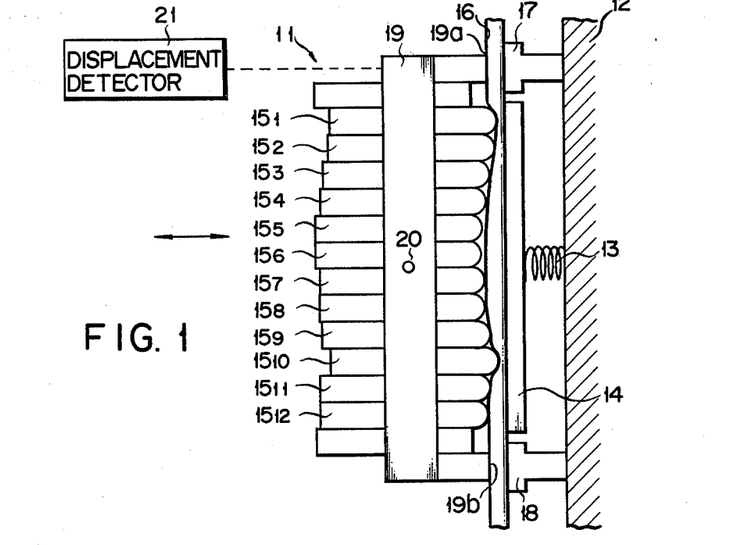
FIG. 1 is a side view of a peristaltic type fluid-infusion pump having an apparatus for detecting occlusion in the peristaltic type fluid-infusion pump according to one embodiment of the present invention.

FIG. 1 shows an apparatus for detecting occlusion provided with a peristaltic type finger pump. A finger pump 11 comprises a pressure plate 14 supported on a base plate 12 by means of a spring 13, and a plurality of fingers $15_1$ to $15_{12}$ disposed in opposition to this pressure plate 14. A tube 16 of soft vinyl chloride of 2.5 mm inner diameter and 4.0 mm outer diameter is interposed between these fingers $15_1$ to $15_{12}$ and the pressure plate 14. Fluid such as a drug inside the tube 16 is delivered by the fingers $15_1$ to $15_{12}$ sequentially pressing the tube 16. Stationary pieces 17 and 18 of the same shape are disposed symmetrically at the inlet section or inlet port and the outlet section or outlet port, respectively, of the peristaltic type finger pump 11. A movable detection piece 19 of the apparatus for detecting occlusion is mounted to press the tube 16 at a predetermined pressure at the inlet port and the outlet port of the pump 11 in cooperation with the stationary pieces 17 and 18. This movable detection piece 19 has a fulcrum 20 at the middle point between the stationary pieces 17 and 18, so that the movable detection piece 19 is pivotable about this fulcrum 20 and presses the tube 16 by pressing parts 19a and 19b which oppose the stationary pieces 17 and 18. A displacement detector 21 for detecting a displacement of the detection piece 19 is coupled to this movable detection piece 19.

Figure 2:
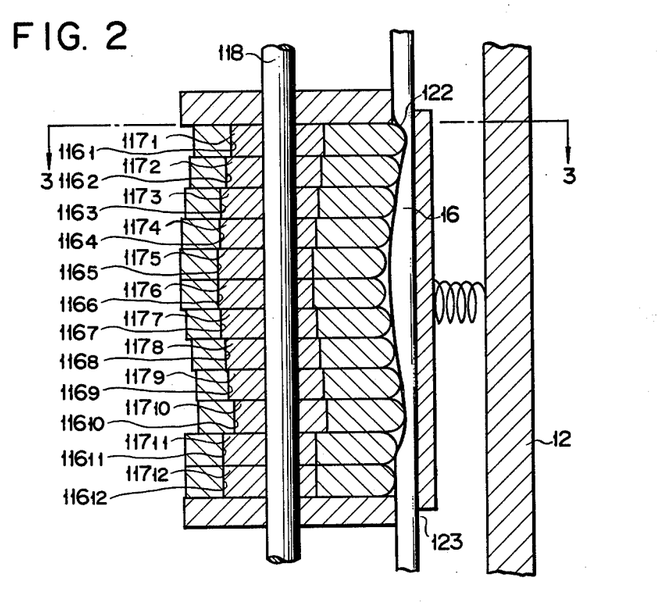
FIG. 2 is a sectional view of the peristaltic type fluid-infusion pump of FIG. 1.
Figure 3:
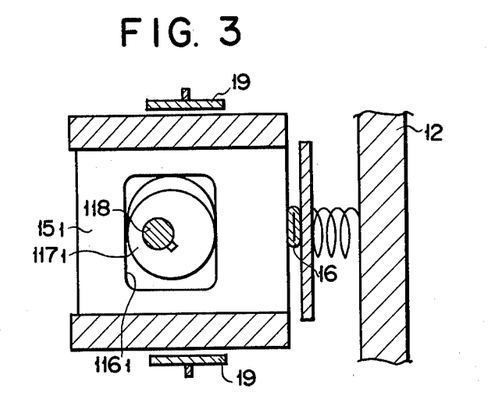
FIG. 3 is a sectional view of the pump along the line 3—3 of FIG. 2.
Figure 4:
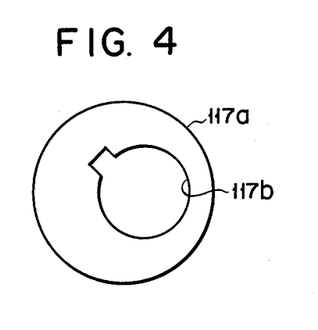
FIG. 4 is a plan view of a fluid-infusion eccentric cam.
Figure 5:
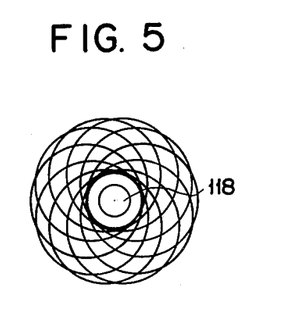
FIG. 5 is a perspective view of superposed fluid-infusion eccentric cams.
Figure 6:
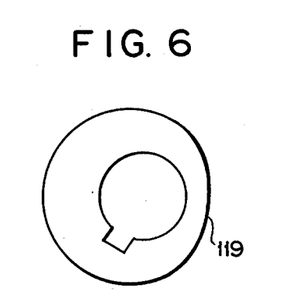
FIG. 6 is a plan view of a pulsation-correction eccentric cam.
Figure 7:
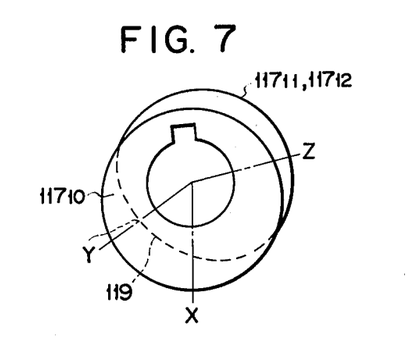
FIG. 7 is a view showing the superposed relation of the fluid-infusion eccentric cam and the pulsation-correction eccentric cams.

FIG. 2 is a transverse sectional view of a peristaltic type finger pump. As may be seen from this figure, rectangular cam holes $116_1$ to $116_{12}$ are formed in the fingers $15_1$ to $15_{12}$. Eccentric cams $117_1$ to $117_{12}$ are respectively housed in these cam holes $116_1$ to $116_{12}$. FIG. 3 is a sectional view along the line 3—3 of FIG. 2. Each of the eccentric cams $117_1$ to $117_{10}$ has a circular cam surface 117a and a shaft hole 117b as shown in FIG. 4 and is mounted on a shaft 118 as shifted through a predetermined angle, for example, 36° from one another as shown in FIG. 5. Eccentric cams $117_{11}$ and $117_{12}$ housed in the pulsation-correction fingers $15_{11}$ and $15_{12}$ have cam surfaces as shown in FIG. 6 designed according to the method to be described below and are mounted on the shaft 118. The strokes of the eccentric cams $117_{11}$ and $117_{12}$ are designed to be shorter than those of the eccentric cams $117_1$ to $117_{10}$. A flat cam surface 119 is arranged at the side of the shortest stroke. The relative positions of the fluid-infusion eccentric cam $117_{10}$ and the pulsation-correction eccentric cams $117_{11}$ and $117_{12}$ are as shown in FIG. 7. Referring to FIG. 7, when the point of the maximum stroke of the eccentric cam $117_{10}$ is defined as X, the point of the shortest stroke, that is, the bottom dead center of the pulsation-correction eccentric cams $117_{11}$ and $117_{12}$ is defined as Y, the point of the maximum stroke, that is, the top dead center of the cams $117_{11}$ and $117_{12}$ is defined as Z, and the middle point of the shaft is defined as O, it is most preferable that the angle XOY is 55° and the angle XOZ is 105.4°.

A tube 16 having an inner diameter of 2.5 mm and an outer diameter of 4.0 mm, for example, is clamped between the fingers $15_1$ to $15_{12}$ and the pressure plate 14. The pressure plate 14 presses the tube 16 toward the fingers $15_1$ to $15_{12}$ by the biasing force of the spring 13 so that the tube 16 is constantly closed by some of the fluid-infusion fingers $15_1$ to $15_{12}$. When the shaft 118 rotates and the cams $117_1$ to $117_{12}$ simultaneously rotate under this condition, the fingers $15_1$ to $15_{12}$ start moving to provide peristalsis to the tube 16. Thus, the fluid-infusion fingers $15_1$ to $15_{10}$ sequentially displace points of closure 121 of the tube 16. The fluid inside the tube is thus delivered from an inlet port 122 to an outlet port 123.

Figure 8:
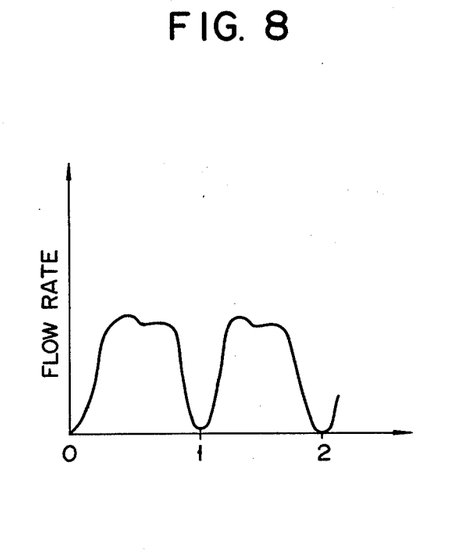
FIG. 8 is a view showing the pulsation waveform of the infusion fluid delivered by the fluid-infusion fingers.
Figure 9:
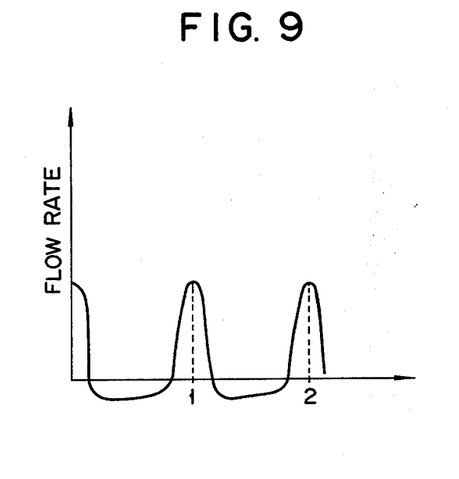
FIG. 9 is a view showing the pulsation waveform of the opposite phase delivered by the pulsation-correction fingers.

When the fluid is fed by the fluid-infusion fingers $15_1$ to $15_{10}$, the flow rate of the infusion fluid changes for the cams $117_1$ to $117_{10}$ as shown in FIG. 8 and provides pulsations. When pulsations opposite to these pulsations (FIG. 9), that is, the pulsations of opposite phases are formed, the waveforms of these pulsations cancel each other so that a constant fluid-infusion waveform may be obtained. According to the present invention, the pulsations of the opposite phases are formed by the pulsation-correction cams $15_{11}$ and $15_{12}$. When the flow rate becomes smaller with the fluid-infusion waveform (FIG. 8) provided by the fluid-infusion fingers $15_1$ to $15_{10}$, the pulsation-correction fingers $15_{11}$ and $15_{12}$ press the tube 16 to increase the flow rate at the outlet port 123 by the amount corresponding to the volume of the crushed tube. In this case, the top dead center Z of the pulsation-correction cams $117_{11}$ and $117_{12}$ presses the pulsation-correction fingers $15_{11}$ and $15_{12}$. When the flow rate becomes great with the fluid-infusion waveform, the pulsation-correction fingers $15_{11}$ and $15_{12}$ gradually withdraw from the tube 16. The correction cams $117_{11}$ and $117_{12}$ rotate such that the position of the top dead center Z is displaced and is replaced by the lower dead center Y. As the pulsation-correction fingers $15_{11}$ and $15_{12}$ are withdrawn, the tube 16 recovers its original shape by its elasticity, thereby reducing the amount of the fluid delivered from the outlet port 123. The flow rate of the infusion fluid fed from the outlet port 123 is kept constant by performing compression and expansion of the tube 16 at the outlet port 123 according to the fluid-infusion waveform.

When fluid infusion is being performed normally in this manner, the pressing parts 19a and 19b at both ends of the movable detection piece 19 equally receive the added pressure of the repelling force of the tube 16 and the internal pressure of the tube. Due to this, the movable detection piece 19 is held at the normal, uninclined position. When occlusion arises, for example, at the outlet port of the pump 11 under this condition, the internal pressure of the tube 11 is raised at the outlet port so that the pressing part 19b at this side is pressed away from the stationary piece 18. As a result, the movable detection piece 19 is pivoted clockwise about the fulcrum 20, and the pressing part 19a at the inlet port presses the tube 16 toward the stationary piece 17. The pivotal movement of the movable detection piece 19, that is, the displacement from its normal position is detected by a displacement detector 21. Based on this displacement detection, the formation of the occlusion is signaled by an alarm device such as a buzzer.

The above description concerns a case wherein the occlusion is formed at the outlet port 123. Since the fluid or drug is not delivered when the occlusion is formed at the inlet port 122, the internal pressure of the tube at the inlet port 122 is reduced. Then, the detection piece 19 is pivoted clockwise as in the above case. The occlusion is thus detected.

Figure 10:
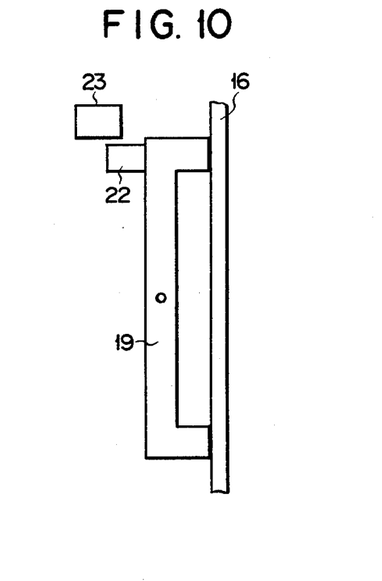
FIG. 10 is a side view of the apparatus for detecting occlusion.
Figure 11:
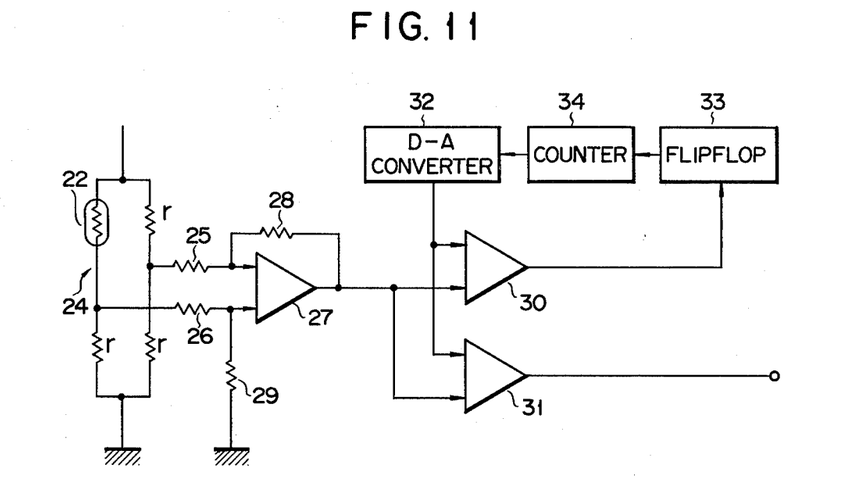
FIG. 11 is a circuit diagram of the apparatus for detecting occlusion.

The detection of the occlusion may thus be performed when the occlusion is formed either at the inlet port or at the outlet port. As the displacement detector 21, a displacement detection member such as a limit switch, a Hall element, a magnetic reluctance element, a strain gauge, or various proximity sensors may be disposed at one end of the detection piece 19 so as to detect the displacement of the detection piece 19. FIG. 10 shows an embodiment wherein a magnetic reluctance element is used as the displacement detection member. According to this embodiment, a magnetic reluctance element 22 is mounted at one end of the detection piece 19, and a magnet 23 is secured near the magnetic reluctance element 22, for example, on a base body. The magnetic reluctance element 22 is connected to a bridge circuit 24 of the detection circuit shown in FIG. 11 as one of the resistance elements connected to it. FIG. 10 shows a case when one magnetic reluctance element 22 is used. When magnetic reluctance elements are used for four sides of the bridge, the detecting sensitivity is improved and adverse effects caused by the temperature changes are cancelled by the opposite sides so that stabler operation may be expected. The output of the bridge circuit 24 is connected to the two inputs of an operational amplifier 27 through resistors 25 and 26, respectively. One input of the operation amplifier 27 is connected to the output through a resistor 28, and the other input is grounded through a resistor 29. The output of the operational amplifier 27 is connected to one input each of comparators 30 and 31. The other inputs of these comparators 30 and 31 are connected to the output of a D-A converter 32. The output of the comparator 30 is connected to a flip-flop 33 whose output is connected to a counter 34. The output of the counter 34 is connected to a D-A converter 32. In the circuit shown in FIG. 11, the comparator 30, the flip-flop 33, the counter 34, and the D-A converter 32 comprise a digital sampling and holding circuit. This sampling and holding circuit is included to store the output level of the operational amplifier 27 obtained under the initial condition, that is, under the condition that no pressure change is present in the tube mounted to the apparatus for detecting occlusion, and also to eliminate the effects of differences in the mounting method of the tube. The comparator 31 is constructed so as to be inverted at a voltage higher than that at which the comparator 30 is inverted. The pressure for detecting the occlusion may be arbitrarily set by adjusting this voltage level.

When the detection piece 19 in FIG. 10 is displaced, the reluctance of the magnetic reluctance element 22 changes according to this displacement. The change in the reluctance is detected by the bridge circuit 24 shown in FIG. 11. The output signal from the bridge circuit 24 is amplified by the operational amplifier 27 and is fed to the comparator 31 where it is compared with a reference signal from the sampling and holding circuit. When the output signal is at a higher level than the reference signal, the output of the comparator 31 is inverted. The inverted output is used to actuate the occlusion alarm device.

Figure 12:
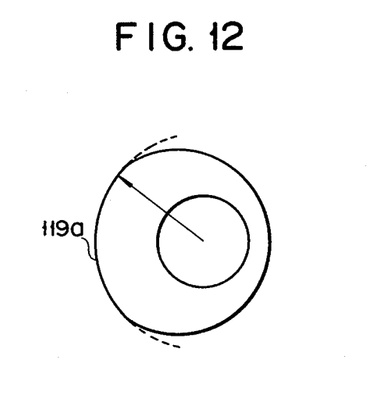
FIG. 12 is a plan view of the fluid-infusion eccentric cams according to a modification of the present invention.

When the shaft 118 rotates under the condition that the finger member $15_1$ closes the tube 16 under pressure in cooperation with the pressure plate 14 at the extreme end of the inlet port 122 in the peristaltic type finger pump as described above, the finger member $15_1$ is withdrawn and the finger member $15_2$ presses the tube 16 in place of it. Since the thickness of the tube 16 is constant, the pressure plate 14 moves as the first finger member $15_1$ withdraws. When the finger member $15_2$ advances to the front of the finger member $15_1$, the pressure plate 14 is returned by the finger member $15_2$. When the shaft 118 rotates further, the finger member $15_3$ replaces the finger member $15_2$ so that the finger member $15_3$ closes the tube 20 by pressure in place of the finger $15_2$. The pressure plate 14 moves in the front-back direction with each replacement among the fluid-infusion finger members $15_1$ to $15_{10}$. Since it is difficult due to various conditions of the design of the cams to eliminate such front-back movement of the pressure plate by the pulsation-correction fingers $15_{11}$ and $15_{12}$ which are driven by the pulsation-correction cams $117_{11}$ and $117_{12}$, it is preferable that the pressure plate never undergo this front-back movement. For this purpose, the fluid-infusion finger cams $117_1$ to $117_{10}$ form an arc-shaped surface 119a corresponding to the arc around the eccentric shaft, as shown in FIG. 12. When cams having such an arc-shaped surface 119a are used, the cams $117_1$ to $117_{10}$, mounted on the shaft 118 as shifted from one other through 36°, form at their peripheries a substantially complete circle. Accordingly, when the fluid-infusion eccentric cams $117_1$ to $117_{10}$ rotate, the finger members $15_1$ to $15_{10}$ will not move to displace the pressure plate 14 in the front-back direction.

The method for producing the shapes of the pulsation-correction cams $117_{11}$ and $117_{12}$ will now be described.

Figure 13:
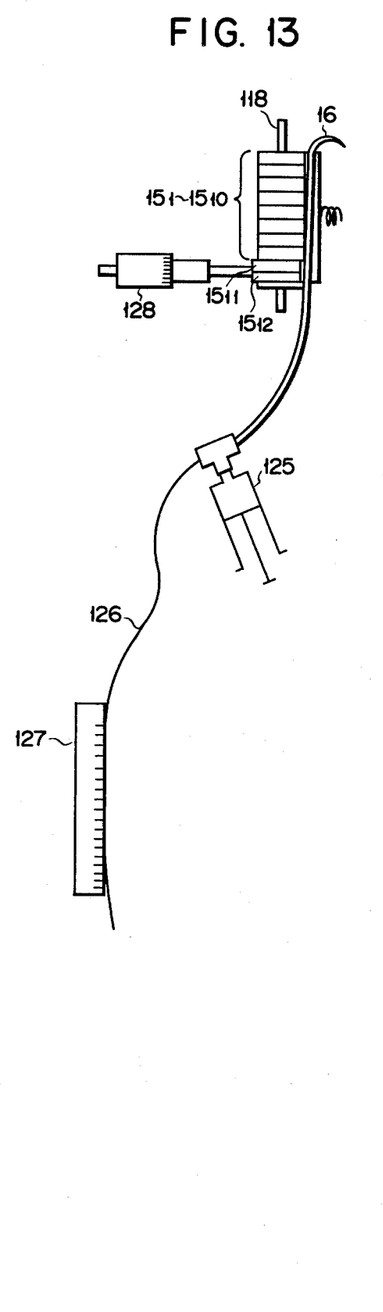
FIG. 13 is a view for explaining the actual measurement method for designing the pulsation-correction eccentric cams.

FIG. 13 shows a method which is based on actual measurements. According to this method, the shaft 118 is rotated through one revolution and the fluid is fed in an amount corresponding to one revolution of the shaft 118 of the finger pump. The fluid fed to the ultrafine tube 126 through a cylinder 125 is measured in units of length, and this length l is divided into segments, for example, n(100) segments. This length l/n is defined as α. The shaft 118 is set to angle 0, and the fluid level inside the ultrafine tube 126 is set to 0 of a scale 127. Under this condition, the shaft 118 is rotated through 360°/n(100), and the pulsation-correction finger members $15_{11}$ and $15_{12}$ are displaced in the front-back direction by adjusting a micrometer 128 so that the fluid level of the ultrafine tube 126 comes to the position of the length α of the scale 127. The indicated value of the micrometer 128 is read when the fluid level of the ultrafine tube 126 is aligned with the reading of α of the scale 127. The piston of the cylinder 125 is moved next, the fluid level of the ultrafine tube 126 is aligned with the value 0 of the scale 127, and the shaft 118 is rotated through 360°/n(100) again. These procedures are repeated until the shaft completes one revolution. The movements of the pulsation-correction finger members are obtained from the micrometer measurements when the shaft completes one revolution. The pulsation-correction finger members are designed based on these measurements.

The method for obtaining the shapes of the correction cams by calculation will be described next. When the tube is crushed in the direction perpendicular to its axis, the cross section of the tube being crushed is first an ellipse, then an extremely elongated circle, and finally comes to resemble eyeglass frames just before the tube is completely crushed. The changes in the shape are different depending upon the material of the tube, the ratio of the wall thickness of the tube to the diameter thereof, and the like. However, the basic tendency seems to be the same. In the case of a peristaltic type fluid-infusion finger pump, changes in the volume within the tube determined by changes in the shape of the tube are greatest when the cross section of the tube is an elongated circle. Accordingly, it is assumed that the volume of the tube changes approximately with the elongated circular cross-sectional area of the tube.

Figure 14:
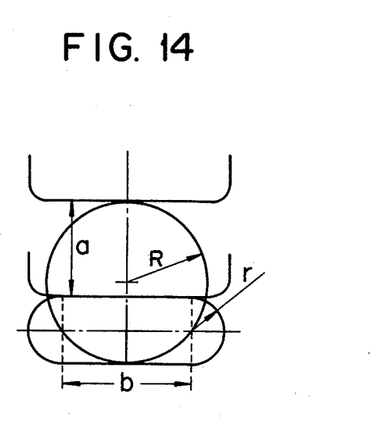
FIG. 14 is a view showing the crushed condition of the tube.

FIG. 14 shows the circular cross section of the tube before it is crushed by the finger members, superposed on the elongated circular cross section of the tube when it is slightly smashed. The cross-sectional area of the tube before crushing is $S_0$, $$S_0 = \pi R^2 \qquad \ldots (1)$$

From FIG. 14, $$2R = a + 2r \qquad \ldots (2)$$

Therefore, $$2\pi R = 2\pi r + 2b \qquad \ldots (3)$$

where a is the diameter reduction of the tube crushed by the finger members, and b is the length of the horizontal part of the elongated circle.

The cross-sectional area of the tube after crushing is S, $$S = \pi r^2 + 2br \qquad (4) \ldots$$

When equations (2) and (3) are substituted into equation (4), this gives $$r = \frac{2R - a}{2} \qquad (2')$$

$$b = \tfrac{1}{2}\pi a \qquad (3')$$

$$S = \pi \left(\frac{2R - a}{2}\right)^2 + \pi a \left(\frac{2R - a}{2}\right) \qquad (5)$$

$$= \pi R^2 - \pi \left(\frac{a}{2}\right)^2 \qquad (5')$$

where a is determined by the angle of the eccentric cam and the eccentricity. When the stroke of the finger member in the front-back direction is 2R, and the tube is assumed to return to its circular shape as the finger member is most withdrawn, the eccentricity of the eccentric cam is R. If the finger member is most withdrawn when the angle of the eccentric cam is 0°, $$a = R - R \cos \theta \qquad (6)$$

where $\theta$ is the angle of the eccentric cam. When equation (6) is substituted into equation (5'), $$S = \pi R^2 - \pi \left( \frac{R - R\cos\theta}{2} \right) \qquad (7)$$

The volume v of the tube crushed by the finger member is obtained by multiplying the thickness t of the finger member by this value, provided that the cross-sectional area of the tube does not change along the axis of the tube. Thus, $$v = t \left\{ \pi R^2 - \pi \left( \frac{R - R\cos\theta}{2} \right) \right\} \qquad (8)$$

The flow rate is obtained by the change in the volume of the tube at the outlet port of the pump. When this finger at the point of closure is the nth finger, the volume of the tube crushed by the finger member is $$V = \sum_{K=n}^{10} t \left\{ \pi R^2 - \pi \left( \frac{R - R\cos\theta K}{2} \right) \right\} \qquad (9)$$

where $\theta$ is 36° assuming the number of finger members is 10. If the value of V is obtained by varying n from 1 through 10, or further dividing 36° for a smaller angle, the volume of the tube for this angle is obtained. The flow rate per angle can thus be obtained by obtaining the difference in the values of V. Although the flow rate thus obtained has pulsations, the movements of the pulsation-correction cams and the finger members are calculated to produce the opposite pulsations.

By using the pulsation-correction cams designed by the measurements or calculations described above, pulsations in the peristaltic type fluid-infusion finger pump are prevented so that constant flow ideal for the fluid-infusion pump may be obtained. Since the pulsation-correction cams may also be mounted on the shaft of the fluid-infusion finger members of the finger pump, the number of required parts may be decreased. Although the present invention has been described as applied to a peristaltic type fluid-infusion finger pump, it is to be understood that the present invention is also applicable to a peristaltic type fluid-infusion roller pump as shown in FIG. 15.

Figure 15:
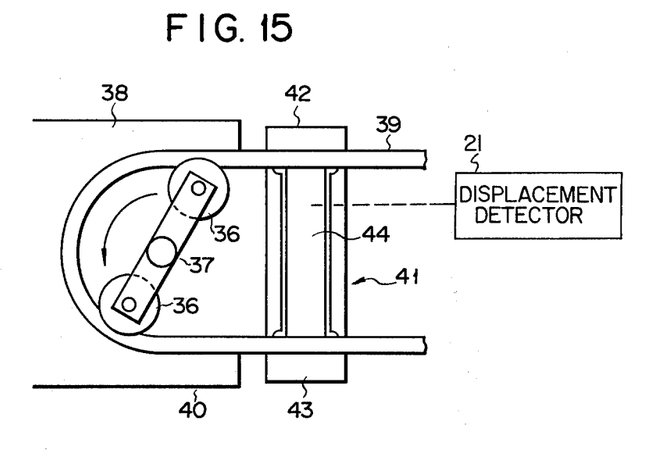
FIG. 15 is a side view of an apparatus for detecting occlusion and a peristaltic type roller pump according to another embodiment of the present invention.

In the embodiment shown in FIG. 15, a tube 39 is interposed between a stator 38 and a rotary body 37 having two rollers 36. The pumping action is effected by squeezing the tube 39 with the rollers 36 when the rotary body 37 rotates in the direction of the arrow. The tube extending from the inlet port to the outlet port of such a roller pump 40 has an apparatus 41 for detecting occlusion. This apparatus 41 for detecting occlusion comprises two stationary pieces 42 and 43, and a movable detection piece 44 which is vertically movably disposed between these stationary pieces and which presses the tube 39 with a predetermined pressure in cooperation with the stationary pieces. A displacement detector 21 similar to that of the embodiment of FIG. 1 is coupled to the movable detection piece 44. According to such a structure, when occlusion is formed at the inlet port, the internal pressure of the tube at the inlet port is reduced. When occlusion is formed at the outlet port, the internal pressure of the tube at the outlet port is raised. In either case, the detection piece 44 is displaced upwardly from its normal position. Therefore, when a displacement detection member is mounted on the detection piece 44, the detection of the occlusion may be performed in a similar manner as in the case of the former embodiment. Furthermore, according to the present invention, the positions and the shapes of the stationary pieces, the detection piece and the other components are symmetrical. Due to this, even when the elasticity of the tube changes at one side due to a temperature change, the elasticity of the other side similarly changes so that the position of the detection piece does not move. Even when the tube undergoes creep strain and the repelling force changes at one side, it changes similarly at the other side, so that the position of the detection piece is not changed.

According to the present invention, occlusion at the inlet port or the outlet port is detected through an increase or decrease in the internal pressure of the tube, so that detection of formation of the occlusion may be performed when the occlusion is formed at either the inlet port or the outlet port. Further, the detection piece moves in the same direction regardless of whether the occlusion is formed at the inlet port or the outlet port, so that detection may be performed with one displacement detector. There is no need to dispose the members for detection of occlusion within the fluid-infusion set for the pump. This poses no danger of contamination of the fluid or drug inside the tube at the part for detection of occlusion since there is no contact with the fluid or drug. The currently used pump may also be used, requiring no extra cost on the pump side. Further, the apparatus may be mounted at any part of the tube. The tube may be made of a material which is relatively inferior in elasticity, such as vinyl chloride. The fluid infusing through the tube may be blood as well as the liquid drug.

What is claimed is:

1. A method for detecting occlusion in a fluid-infusion tube of a peristaltic fluid-infusion pump, comprising:

pressing respective wall portions of the fluid-infusion tube on inlet and outlet sides of the pump with substantially equal pressures during normal fluid infusing, by means of pressing means which includes a pair of pressing parts on a common movable member;

detecting a change in the position of said common movable member of said pressing means, said change being a result of a change in the difference between a first distance and a second distance, said first distance being defined by the distance between opposite wall portions of the fluid-infusion tube at said inlet side and being a function of the fluid pressure in the inlet portion of the tube; and said second distance being defined by the distance between opposite wall portions of the tube at said outlet side and being a function of the fluid pressure in the outlet portion of the tube, the sum of said first and second distances always being constant; and detecting an occlusion in the fluid-infusion tube from said detected change in position.

2. An apparatus for detecting occlusion in a fluid-infusion tube of a peristaltic fluid-infusion pump comprising:

a pair of stationary pieces respectively mounted adjacent said fluid-infusion tube at a fluid inlet portion and a fluid outlet portion of said fluid-infusion pump;

a common movable member having a pair of pressing parts disposed respectively in opposition to said stationary pieces, said pressing parts being adapted to press the parts of said fluid-infusion tube which correspond to said fluid inlet and outlet portion of said pump, with a predetermined substantially equal pressure between said pressing parts and said respective associated stationary pieces during normal fluid infusing, said common movable member being adapted to be displaced corresponding to a change in a first distance between opposite wall portions of said fluid-infusion tube at said inlet portion thereof, and a change in a second distance at said outlet portion thereof, the sum of said first and second distances always being constant, said first and second distances being changed by a change in the internal pressure of said fluid-infusion tube caused by occlusion in said fluid-infusion tube; and means coupled to said common movable member for detecting said occlusion by detecting said displacement of said common movable member.

3. An apparatus according to claim 2, wherein said common movable member has a fulcrum, and said pressing parts are on opposite sides of said fulcrum, said pressing parts being pivotable about said fulcrum in opposite directions.

4. An apparatus according to claim 3, wherein said common movable member comprises a single elongated rigid member pivotally mounted about said fulcrum, and wherein said pressing parts are on opposite ends of said elongated member and are arranged in opposition to respective stationary pieces.

5. An apparatus according to claim 2, wherein said means for detecting occlusion is mounted at one end of said common movable member and comprises a displacement detection element actuated in response to a displacement of said common movable member.

6. An apparatus according to claim 5, wherein said displacement detection element comprises a proximity sensor mounted near said common movable member.

7. An apparatus according to claim 2, wherein said means for detecting occlusion comprises:

a magnetic reluctance element mounted at one end of said common movable member;

a magnet arranged near said magnetic reluctance element;

a bridge circuit including said magnetic reluctance element for providing an output signal corresponding to the reluctance of said magnetic reluctance element;

a sampling and holding circuit coupled to said bridge circuit for storing, as a reference signal, the initial output signal level of said bridge circuit; and a comparator coupled to said sampling and holding circuit for comparing said reference signal from said sampling and holding circuit with the output signal from said bridge circuit.

8. An apparatus according to claim 7, comprising alarm output means coupled to an output of said comparator for providing an alarm signal.

9. An apparatus according to claim 2, wherein said common movable member is disposed between said stationary pieces such that it is capable of reciprocating movement between said stationary pieces.

10. An apparatus according to any one of claims 2, 3, 5, 6, 7 or 8, wherein said peristaltic fluid-infusion pump includes a plurality of finger members for generating peristalsis in said fluid-infusion tube.

11. An apparatus according to any one of claims 2, 5, 6, 7, 8 or 9, wherein said peristaltic fluid-infusion pump comprises a peristaltic roller pump which in turn comprises a stator and a rotary body having two rollers, said fluid-infusion tube being clamped between said stator and said rotary body, and fluid infusion is performed by rotation of said rotary body.

12. An apparatus according to claim 2 or 3, wherein said common member is a single elongated rigid member, and said pressing parts extend from said elongated rigid member at opposite end portions thereof.

13. An apparatus according to claim 2, wherein said pressing parts comprise end portions of said common movable member.

14. An apparatus according to claim 13, wherein said stationary pieces are disposed opposite and spaced from respective ends of said common movable member.

15. An apparatus according to claim 13 or 14, wherein said common movable member is an elongated rigid member movable in the longitudinal direction thereof.

* * * * *